(12) United States Patent
Boese et al.

(10) Patent No.: US 8,750,582 B2
(45) Date of Patent: Jun. 10, 2014

(54) METHOD FOR RECORDING AND RECONSTRUCTING A THREE-DIMENSIONAL IMAGE DATASET AND X-RAY APPARATUS

(75) Inventors: Jan Boese, Eckental (DE); Anja Borsdorf, Erlangen (DE); Frank Dennerlein, Forchheim (DE); Holger Kunze, Bubenreuth (DE)

(73) Assignee: Siemens Aktiengesellschaft, München (DE)

( * ) Notice: Subject to any disclaimer, the term of this patent is extended or adjusted under 35 U.S.C. 154(b) by 510 days.

(21) Appl. No.: 13/101,208

(22) Filed: May 5, 2011

(65) Prior Publication Data

US 2011/0274335 A1     Nov. 10, 2011

(30) Foreign Application Priority Data

May 6, 2010 (DE) .......................... 10 2010 019 632

(51) Int. Cl.
  *G06K 9/00*     (2006.01)
(52) U.S. Cl.
  USPC ........................... 382/128; 382/131; 382/132
(58) Field of Classification Search
  USPC ............................................... 382/128, 154
  See application file for complete search history.

(56) References Cited

U.S. PATENT DOCUMENTS

| 6,782,137 | B1 | 8/2004 | Avinash |
| 6,788,759 | B2 * | 9/2004 | Op De Beek et al. .......... 378/19 |
| 6,810,278 | B2 * | 10/2004 | Webber et al. ................ 600/407 |
| 7,142,633 | B2 * | 11/2006 | Eberhard et al. ................ 378/62 |
| 7,604,404 | B2 * | 10/2009 | Ohishi et al. .................. 378/197 |

FOREIGN PATENT DOCUMENTS

| DE | 10305221 A1 | 8/2004 |
| DE | 102006041033 A1 | 3/2008 |

OTHER PUBLICATIONS

Zellerhoff et al.; "Low contrast 3D reconstruction from C-arm data", Proceedings of the SPIE, Medical Imaging 2005, vol. 5745, pp. 646-655; Magazine; 2005.
Gonzalez et al. "Digital image processing" Rafael C. Gonzalez, Richard E. Woods, Addison-Wesley, 1992, pp. 187-189; Book; 1992.
Buzug Einführung in die Computertomographie / Mathematisch-physikalische Grundlagen der Bildrekonstruktion 1. Nachdruck 2005 pp. 398-400; Book; 2005.
Borsdorf et al., "Separate CT-Reconstruction for 3D Wavelet Based Noise Reduction Using Correlation Analysis"; IEEE Nuclear Science Symposium Conference Record pp. 2633-2638; Magazine; 2007.
Lifeng Yu et al.; "Sinogram Smoothing with Bilateral Filtering for Low-dose CT"; Medical Imaging 2008: Physics of Medical Imaging, edited by Jiang Hsieh, Ehsan Samei, Proc. of SPIE, vol. 6913, (2008) pp. 691329-691329-8; Magazine; 2008.
Buades et al. "Topology preserving linear filtering applied to medical imaging" SIIMS (1) pp. 26-50; Magazine; 2008.

* cited by examiner

*Primary Examiner* — Tom Y Lu

(57) ABSTRACT

A method for recording and reconstructing a three-dimensional image dataset is proposed. A plurality of projection images are acquired under different recording geometries in relation to an object to be recorded by an X-ray apparatus, in particular a C-arm X-ray apparatus. At least two projection images are recorded for at least one recording geometry, in particular for every recording geometry. The three-dimensional image dataset is reconstructed from the project images.

14 Claims, 3 Drawing Sheets

METHOD FOR RECORDING AND RECONSTRUCTING A THREE-DIMENSIONAL IMAGE DATASET AND X-RAY APPARATUS

CROSS REFERENCE TO RELATED APPLICATIONS

This application claims priority of German application No. 10 2010 019 632.0 filed May 6, 2010, which is incorporated by reference herein in its entirety.

FIELD OF THE INVENTION

The invention relates to a method for recording and reconstructing a three-dimensional image dataset from projection images recorded under different recording geometries in relation to an object that is to be recorded by means of an X-ray apparatus, in particular a C-arm X-ray apparatus, a recording geometry being defined by a specified geometric position and orientation of X-ray tube assembly and X-ray detector, as well as to an associated X-ray apparatus.

BACKGROUND OF THE INVENTION

Modern X-ray systems, in particular modern C-arm X-ray systems having flat-panel detectors have now become established as part of standard practice in medical imaging, in particular also in interventional medical imaging. In addition to traditional projection imaging (radiography/fluoroscopy) these systems also support a mode similar to computed tomography in which a sequence of two-dimensional projection images from a sufficiently large number of different projection directions (which consequently describe a specific recording geometry) is converted into a three-dimensional image dataset. For example, the projection images can be recorded during a rotary movement of the on which an X-ray tube assembly and a detector are disposed opposite each other.

By means of such a 3D mode it is possible to reconstruct from a single rotation datasets which cover a large region of an object, for example a complete human cranium, and which offer a high spatial resolution in particular in comparison with diagnostic computed tomography. It is, however, disadvantageous that compared with conventional computed tomography the datasets have a lower contrast resolution and a lower contrast-to-noise ratio which for example may not be sufficient to preclude cerebral hemorrhages with certainty. Cerebral hemorrhages constitute a structure having an extremely low contrast which can be resolved only with difficulty by means of the C-arm X-ray apparatuses.

In three-dimensional C-arm imaging, as already described, the data recording consists in most cases, and in particular also in low-contrast applications, of a single rotary movement around the patient or, as the case may be, the object that is to be recorded. In order to improve the three-dimensional image quality in respect of the low contrasts several methods have hitherto been proposed in the prior art in order to improve the image quality.

Thus, noise reduction methods have been used both on the projection data and in the reconstructed image volume, for example noise reduction of the projection data at the same time as edge enhancement by means of bilateral filters or median filtering or noise reduction in the reconstructed image volume by means of non-linear filtering, for example median filters.

Another approach has been imported from the field of computed tomography and applied also to the three-dimensional reconstruction in C-arm X-ray apparatuses, namely the separation of the recorded projection images into disjoint subsets and the reconstruction of reconstruction datasets from in each case one of said subsets. The partial results are subsequently combined non-linearly to form a quality-enhanced image volume, an efficient approach relating to a wavelet-based fusion of two separately reconstructed datasets by means of correlation analysis; cf. in this regard for example the article by A. Borsdorf et al, "Separate CT Reconstruction for 3D Wavelet Based Noise Reduction Using Correlation Analysis", in Yu, Bo (Eds.), IEEE NSS/MIC Conference Record (WEE Nuclear Science Symposium and Medical Imaging Conference, Honolulu, USA, Oct. 27-Nov. 3, 2007), 2007, pages 2633 to 2638.

DE 10 2006 041 033 A1 relates to a method for reconstructing a three-dimensional image volume by means of a virtual extension of the X-ray detector. In the examination of certain body regions a specified maximum width can be exceeded. For this purpose it is proposed to record two or more individual projection images at each curve plot-point of the trajectory, which images can be assembled into an extended projection image. The same recording geometry is therefore not present. The images must be different in terms of their recording regions to enable a virtual extension of the X-ray detector to be possible at all.

However, a disadvantage of these methods is that contrasts that are lost in individual projection images cannot be reinstated either by operations in the projection image or by operations in the image space.

SUMMARY OF THE INVENTION

The object underlying the present invention is therefore to disclose a method for recording and reconstructing a three-dimensional image dataset which permits improved imaging in relation to low-contrast structures in particular by means of a C-arm X-ray apparatus.

In order to achieve this object it is inventively provided in the case of a method of the type cited in the introduction that in at least one recording geometry, in particular every recording geometry, at least two projection images are recorded and taken into account in the reconstruction, a plurality of projection images (P1 . . . PM) of a recording geometry being acquired using different recording parameters.

The basic concept of the present invention is to acquire, not one, but a plurality of projection images for realizing an improved image quality in the low-contrast range in the determination of three-dimensional image datasets by means of C-arm X-ray apparatuses for at least one, in particular, however, for every recording geometry of a three-dimensional scan. This is because in this way different sets of information that can be processed collectively are acquired in the corresponding recording geometries, permitting noise and/or artifact reduction in the final reconstruction result by means of correct, in particular adaptive combination into an overall set of information. By means of such a combination mechanism it is possible in particular to take into account the plurality of projection images and to perform their fusion in order to produce a single image dataset in such a way that what is involved is a pre-processing or post-processing, yet the actual reconstruction algorithm—a multiplicity of such being known in the prior art—can remain unchanged. Then the innovative approach proposed here can be combined with any reconstruction method, filtered back-projection for example.

In a first alternative it can be provided that a predetermined number of at least two projection images, in particular 30 to 50, can be recorded for each recording geometry. In this case it is therefore predefined how many projection images are to be recorded in which recording geometry and to be taken into account subsequently. In this case the same predetermined number can be specified for every recording geometry, though it is also conceivable in specific scanning trajectories to record more projection images in some regions, and fewer projection images in other regions.

In an alternative embodiment it can be provided that the number of images to be recorded for a recording geometry is determined adaptively during the recording session, in particular taking into account a dose measurement and/or an image analysis of a first recorded projection image, and/or taking into account information concerning the object to be recorded, in particular the path length through the object in the recording geometry. It is therefore possible, for each recording geometry, to adaptively adjust the number of projection images to be recorded there, wherein firstly preliminary information can be used, for example such information as concerns the object that is to be recorded, from which it emerges how long the path length of the X-ray radiation in the object is likely to be, so that for example in regions in which the path length is very long, and consequently the attenuation very great, the number of projection images to be produced can be increased. In addition or alternatively, however, it is also possible to specify the number of projection images still to follow during the recording itself, for example by considering the dose received in the specific recording geometry. A dose measuring device is already provided in many X-ray apparatuses in order to enable automatic dose regulation to be performed. From the dose it can also be derived, for example, how strong is the attenuation due to the object and whether a particularly low signal-to-noise ratio is to be expected so that then a plurality of projection images can be recorded. Such information can also be deduced from an image analysis which can relate, for example, also to the total dose received by the detector. In this way it is therefore possible to bring about improvements in the most recently obtained image quality at the points at which a particularly poor contrast or a particularly high signal-to-noise ratio is to be expected by recording an especially large number of projection images adapted to the current situation.

It can particularly advantageously be provided that the plurality of projection images of a recording geometry are recorded using different X-ray spectra and/or exposure times and/or filtering parameters. Such an embodiment is beneficial in particular when specific edges/contrast changes or the like are visible only under certain settings and then subsequently supplementary steps can be taken to produce an overall image exhibiting better quality. In this way it is advantageously possible also to achieve an increase in the grayscale value dynamics. In this case it can certainly be possible in the method according to the invention that when specific recording parameters are used images can also be recorded which basically would be diagnostically unusable but in certain sub-regions reveal information that it would not have been possible to obtain with the usual recording parameters. An example of this are overexposed images in which, for example, an area of particularly strong attenuation or path length is present centrally, yet it can nonetheless be well resolved in the image or the like.

The different projection images of a recording geometry can be recorded during a single period in which a recording arrangement of the X-ray apparatus remains in the recording geometry and/or during a plurality of passes of the recording arrangement through the recording geometry. In the example of the C-arm system this means that for example all images can be recorded during a single revolution of the C-arm if a single assumption of the recording geometry is to be sufficient for recording all the images. Using a single recording movement can make sense if the number of recorded projection images varies with the recording geometry. The presence of motion artifacts can be also minimized with only a single recording movement. Nonetheless, a multiple recording movement can also be useful, for example when a constant number of projection images are to be acquired and at least the target volume in the object exhibits little or no movement, in particular is well fixed. For example, it can advantageously be provided that the C-arm performs the standard recording movement around the object multiple times, e.g. as a sequence of forward and backward passes.

In a particularly advantageous embodiment of the method according to the invention it can be provided that the plurality of projection images of one recording geometry are fused in at least one combination step to form at least one combination image and/or at least two reconstruction datasets are determined from different projection images and/or combination images and the image dataset is consolidated herefrom. According to the invention the described combination or fusion of the different projection images can therefore be carried out already on the basis of the projection images themselves, which is preferred according to the invention, and/or also through reconstruction of different reconstruction datasets and their combination. In order to keep the reconstruction overhead to a minimum and to be able to work already at the level of the projection images where certain occurring effects impairing the image quality in the low-contrast range can be handled better, it is advantageous to provide in every case a combination step in which combination images are fused. It is particularly advantageous in this case if at least two different combination steps are performed. This means that different methods for combining or fusing the projection images/combination images can be applied in order to improve the image quality in different ways, as will be discussed in greater depth below. This can additionally, if it is beneficial, be supplemented in that in actual fact more than one reconstruction dataset is produced, these reconstruction datasets then being combined to form the image dataset in a further method for improving the image quality, particularly in relation to the low-contrast range.

Let it also be noted at this point that the processing, in particular the fusion, of the projection images can take place on the basis of the grayscale values, in other words the actual measured data, or on the basis of the line integrals determined therefrom. This can depend in particular on the method used for combining the projection images.

It can beneficially be provided that at least one fusion is performed taking into account the local noise and/or the local image structures. As already mentioned, different priorities on the basis of which image quality is improved can be set in the combination steps or, as the case may be, in the fusion of the image dataset from reconstruction datasets. It is particularly useful in this case to take the local noise into account and as far as possible to identify and reduce it in order to be able to create a higher signal-to-noise ratio and consequently a better contrast-to-noise ratio. Local image structures can equally be taken into account, in particular with regard to whether they appear in a plurality of images, so that in this way artifacts, for example, can be excluded.

In concrete terms it can for example be provided that in the or a combination step at least some of the projection images or the combination images of a recording geometry that were determined in a preceding combination step, in particular projection images recorded using different recording parameters, can be fused into a combination image by means of linear combination. Images, in particular such images as were recorded using different recording parameters, are consequently merged by means of a linear combination into an enhanced projection image, the combination image. In this case it can be provided in particular that the coefficients of the linear combination are selected by means of an optimization algorithm, in particular with regard to a minimized variance of the image data of the combination image. This variant of a combination step can therefore be performed with particular advantage with regard to an optimization of the noise or, as the case may be, the reduction of noise effects. The core concept of the procedure is then that the data from the projection images having a higher signal-to-noise ratio is incorporated to a greater extent into the combined result than the data from the projection images having a lower signal-to-noise ratio. Different coefficients of the linear combination can be used for different images or image regions or image elements (pixels). This means not only that the images can be weighted by means of the coefficients, but also that, in particular also in conjunction with an optimization method directed toward minimizing the noise, local effects can be taken into account, in particular therefore also a local signal-to-noise ratio. It should be pointed out that self-evidently other criteria for an optimization method are also conceivable in principle.

In addition or alternatively it can be provided that the following steps are performed in the or a combination step:
wavelet decomposition of at least some of the projection images or combination images of a recording geometry that were determined in a preceding combination step as input images,
subdivision of the structures determined by means of the wavelet decomposition and described by means of wavelet coefficients in structures contained in all or most of the input images and/or in structures not contained in all or most of the input images by means of a correlation analysis, and
generation of a combination image using the wavelet coefficients describing the structures present in all or most input images.

This variant therefore exploits the basically known fact that wavelet decomposition can be used to describe structures in the input images by means of the resulting wavelet coefficients. These structures can then be classified and identified in a known manner and a check can be performed to determine whether they occur, if not in all, then at least in most of the input images. The basic idea behind this procedure is to identify structures that are contained only in individual projection images or combination images of an identical recording geometry as artifacts resulting due to noise effects, scatter effects or other effects, scatter patterns for example, and to eliminate them to the greatest possible extent in the further processing. In addition to the noise or scatter cited by way of example, such artifacts can also have their cause in other effects, for example readout errors or the like. The limit that indicates in how many input images a structure must be contained in order not to be deemed an artifact should not be set too low. For example, it can be required that if the structures do not have to be present already in every one of the images (equivalent to 100%) that the structures to be retained must be present in at least 90% or 95% of the images. Once all of the structures have been identified in this way as artifact or non-artifact, a single combination image can be synthesized from the corresponding wavelet coefficients using the common structures in each case and with suppression of the different structures.

As already described, it is conceivable to combine several methods, in particular the two combination steps described here, in order to form a two-stage process. The concept of the two-stage process is to be understood in this context as meaning that the existing projection images of a recording geometry are initially combined in a combination step into a smaller number of quality-enhanced combination images, which quality-enhanced combination images are subsequently fused in the combination step using the other method to form a single combination image or a few combination images of said recording geometry, which image or images is or are again enhanced in quality.

As already mentioned, it can alternatively, though preferably additionally, also be provided to generate more than one, possibly already quality-enhanced, reconstruction dataset from the acquired projection images so that at the end a plurality of image volumes have been generated. In order to fuse the plurality of reconstruction datasets it can then be provided that the following steps are performed:
wavelet decomposition of at least some of the reconstruction datasets,
subdivision of the structures determined by means of the wavelet decomposition and described by means of wavelet coefficients in structures contained into all or most of the reconstruction datasets and/or structures not contained in all or most of the reconstruction datasets by means of a correlation analysis, and
generation of the image dataset using the wavelet coefficients describing the structures present in all or most of the reconstruction datasets.

The approach here is therefore similar to that already discussed in relation to the second specifically described variant of the combination step in that ultimately a check is carried out to determine which structures can be classified as noise or scatter artifacts or artifacts based on other effects. In this case, however, the procedure is performed here at the level of the three-dimensional data, i.e. following the reconstruction. An approach of this kind is known in similar fashion already from the article by A. Borsdorf et al cited in the introduction. There, however, the recording geometries are subdivided into disjoint groups, whereas here it is possible to generate complete reconstruction datasets from the recording geometries and compare them with one another in the manner described.

In addition to the method the present invention also relates to an X-ray apparatus, in particular comprising a C-arm, having a control device embodied for performing the method according to the invention. In other words the control device of the X-ray apparatus is embodied in such a way that it can control a recording arrangement during a single three-dimensional scan such that at least two projection images are recorded for at least one recording geometry, which images are then taken into account during the reconstruction. All statements made in relation to the method according to the invention can be applied analogously to the X-ray apparatus according to the invention, so the advantages cited in the introduction can also be achieved therewith.

BRIEF DESCRIPTION OF THE DRAWINGS

Further advantages and details of the present invention will emerge from the exemplary embodiments described hereinbelow as well as with reference to the drawing, in which.

DETAILED DESCRIPTION OF THE INVENTION

Figure 1:
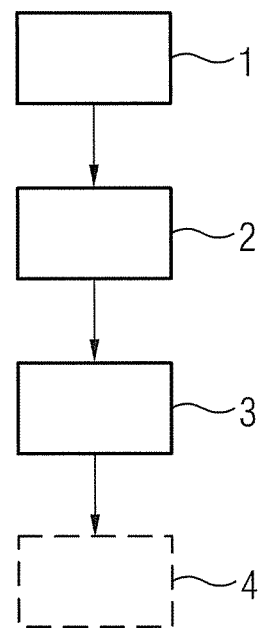
FIG. 1 is a block diagram to illustrate the general flow sequence of the method according to the invention.

FIG. 1 shows a basic flowchart of the method according to the invention for the exemplary embodiments described here. In a step 1 the projection data is acquired in the form of projection images. This is accomplished in such a way that following completion of the recording operation for all or almost all recording geometries that are to be used for recording the three-dimensional image dataset, more than one projection image, for example 30 to 50 projection images, is present. In this context a recording geometry is to be understood as meaning a defined geometric position and orientation of X-ray tube assembly and X-ray detector. For the sake of simplicity it will be assumed for the following discussion of the exemplary embodiments that for each recording geometry a fixed number of projection images that is the same for all recording geometries will be recorded.

It should be pointed out, however, that this does not have to be the case, but instead that it is also possible, in particular within the scope of the method according to the invention, to decide adaptively and during the recording session how many images are to be recorded, for example on the basis of a dose measurement. It is, however, also possible to use information relating to the object that is to be recorded in order to specify from the outset how many projection images are to be recorded from which recording geometry so that, for example, in the case of a longer path length through the object and a likely stronger attenuation, in other words a higher signal-to-noise ratio, more projection images can be recorded under recording geometries of said kind. If this procedure is followed, the approaches described in the following should be adapted in such a way that it will nonetheless be possible to process the projection images in a similar manner with the aim of achieving the desired reconstruction result even if different numbers of projection images exist for the different recording geometries.

The actual recording of the projection images in step 1 can take place in different ways. Whereas it can be provided that all projection images of a recording geometry are recorded during a single recording movement, for example a single rotary movement of a C-arm, in that the C-arm is always briefly stopped for example, it is nevertheless also conceivable, in particular in the present case of a given constant number of projection images, to perform this within the framework of a plurality of standard recording movements of the C-arm, for example during a sequence of forward and backward passes. A combination can also be used in the approach, for example one forward and one backward pass in the course of 30 projection images, with 15 projection images being recorded in each case during the forward and the backward pass.

It is, however, relevant that in the present exemplary embodiment at least some of the projection images of a recording geometry are recorded using different recording parameters, in particular in relation to the X-ray spectrum and the exposure time, in order thereby to increase the grayscale value dynamics in the further course of the method and also to enable structures to be identified which are clearly visible only under certain conditions.

Upon completion of step 1 there is therefore a constant number of projection images available for each recording geometry.

In a step 2 the projection images are then fused to form at least one combination image. One or more combination steps can be provided for this purpose, and one or more combination images can be produced per recording geometry. While details in this regard will be explained more thoroughly later with reference to FIGS. 2-4, the two basic approaches employed in this exemplary embodiment shall be explained in more detail at this point.

A or the combination step can be embodied in this case in such a way that at least some of the projection images and/or combination images already determined in a preceding step, in particular such images that were recorded using different recording parameters, are consolidated by means of a linear combination to produce an enhanced projection, i.e. a new combination image. In this case the coefficients chosen for the linear combination can vary from pixel to pixel or from image region to image region, in a simple exemplary embodiment also from image to image, and are determined within the scope of an optimization algorithm in such a way that the variance (the noise) is minimized in the combination image produced as the result. In this case data from projection images or from combination images produced in a preceding combination step and having a higher (local) signal-to-noise ratio are incorporated to a greater degree into the combination image that is to be produced than data from projection images or combination images having a lower (local) signal-to-noise ratio.

In addition to this possibility of a linear combination as combination step it is also possible in the exemplary embodiments discussed here to work with wavelet decomposition. In this case the said wavelet decomposition of the projection images or of combination images determined in a preceding combination, which for simplicity are to be referred to here as input images, is performed first. Subsequently it is possible to discriminate between structures that are present in most or all of the input images, and changing structures which are to be found only in individual or very few input images, and specifically by means of a correlation analysis in the wavelet coefficients. Structures that occur only in isolated or individual input images can be classified as artifacts and are excluded from further consideration. For the input images, a single combination image for this recording geometry is then synthesized from the corresponding wavelet data using the common structures in each case and by suppressing the different structures. Noise or scatter pattern structures can largely be eliminated in this way.

In summary, therefore, at least one combination image is determined in step 2 through application of at least one combination step to at least some of the projection images. The combination can in this case be performed either in the intensity values, which essentially describe the incident energy per detector pixel, or in the line integral values, which describe the integral density of the object along the X-ray beams.

There are also a number of options in relation to step 3. In each case at least one reconstruction of a three-dimensional dataset is performed there by means of a standard reconstruction method, for example filtered back-projection. In the exemplary embodiments presented here there are two possibilities in this case: On the one hand, if the result of step 2 is just one combination image for each recording geometry, the result of the method, namely the three-dimensional image dataset, can be obtained immediately. If, on the other hand, there are at least two combination images as the result of step 2 for each recording geometry, then a plurality of reconstruction datasets will be reconstructed in step 3, these being processed further in an optional step 4.

If an optional step 4 is provided, the wavelet decomposition is applied there analogously to the three-dimensional reconstruction dataset, which means that in this case, too, the corresponding wavelet coefficients are used and it is established, by means of a correlation analysis, which structures are common to the reconstruction datasets and which are possibly attributable to artifacts. Analogously to the aforementioned combination step, a three-dimensional image dataset is then fused accordingly from the matching structures.

Actual variants of the method according to the invention will now be described with reference to FIGS. 2 to 4.

Figure 2:
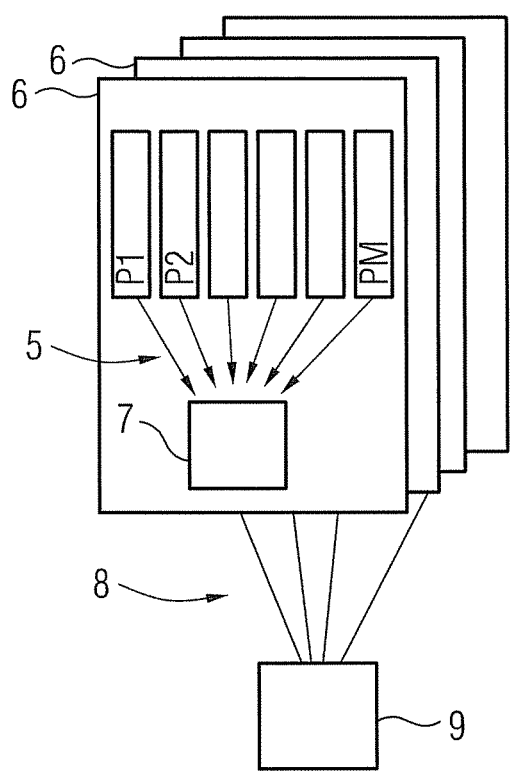
FIG. 2 is an illustration relating to a first embodiment variant of the method according to the invention.

FIG. 2 shows a variant in which only one combination step 5 is used, in which case this can be the linear combination or the wavelet decomposition. Reference sign 6 schematically denotes individual recording geometries. M projection images P1 to PM were recorded in the recording geometry 6 shown in the foreground. Said images are fused in combination step 5 to form a single combination image 7 for said recording geometry 6. The combination images 7 thus produced for each recording geometry 6 are then reconstructed in a reconstruction step 8 to create the image dataset 9, for example by means of filtered back-projection.

Figure 3:
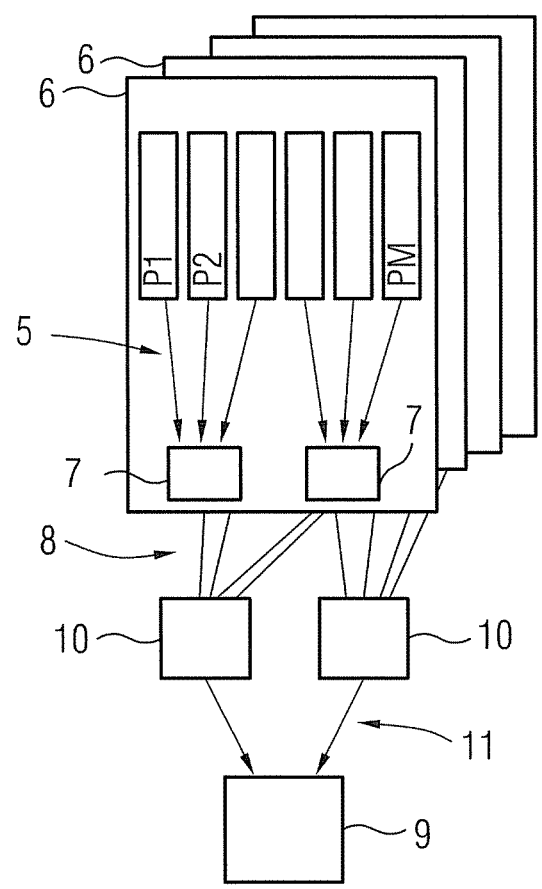
FIG. 3 is an illustration relating to a second embodiment variant of the method according to the invention.

Another embodiment variant is shown in FIG. 3. Once again, M projection images P1 to PM were recorded in the recording geometry 6 shown in the foreground. In this case only a single combination step 5 is again provided in which, however, half of the projection images P1 to PM/2 and PM/2+1 to PM are in each case fused into a combination image 7 in each case, where once again the combination step "linear combination" or the combination step "wavelet decomposition" can be used. It is also conceivable to apply the linear combination method for one half, and the wavelet decomposition method for the other half in combination step 5.

Finally, therefore, there exist two combination images 7 for each recording geometry 6. Accordingly, in reconstruction step 8, two reconstruction volumes 10 are reconstructed here using the two combination images 7 for each recording geometry 6. Said two reconstruction volumes 10 are then fused, as described above, in a fusion step 11 corresponding to the optional step 4 in accordance with the described structure analysis, to form the three-dimensional image dataset 9.

Figure 4:
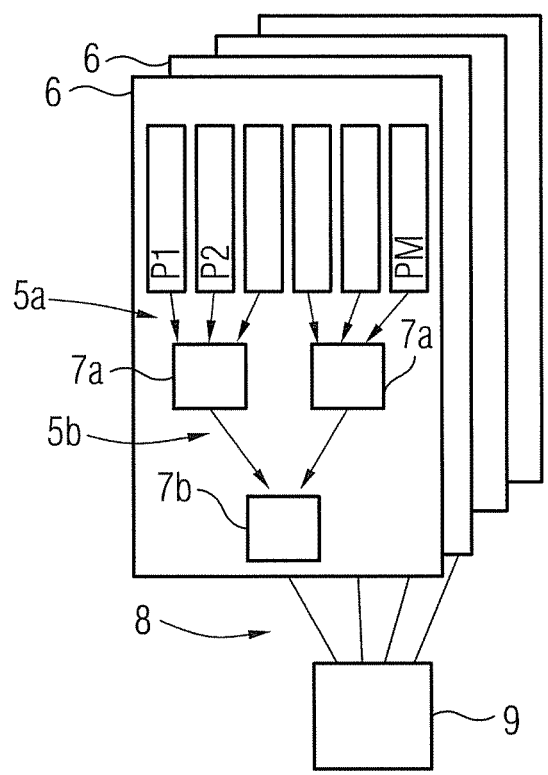
FIG. 4 is an illustration relating to a third embodiment variant of the method according to the invention.

A particularly beneficial variant of the method according to the invention is shown in FIG. 4. There, two combination steps 5a, 5b are provided, the first combination step 5a, which can for example use the linear combination method, supplying intermediate combination images 7a for the recording geometry. Although only two combination images 7a are shown in FIG. 4, it is, of course, also possible to generate more combination images 7a. In the present example said combination images 7a then serve as input images for combination step 5b, which can then use the wavelet decomposition method and structure analysis, for example. The result of combination step 5b is then a single combination image 7b for each recording geometry 6. In reconstruction step 8 this combination image 7b then serves in turn for reconstructing the three-dimensional image dataset 9.

It should be emphasized that other combinations of the described combination steps and further combination steps and fusion steps are, of course, also conceivable in addition to the exemplary embodiments of the method according to the invention shown in FIG. 2 to FIG. 4.

Figure 5:
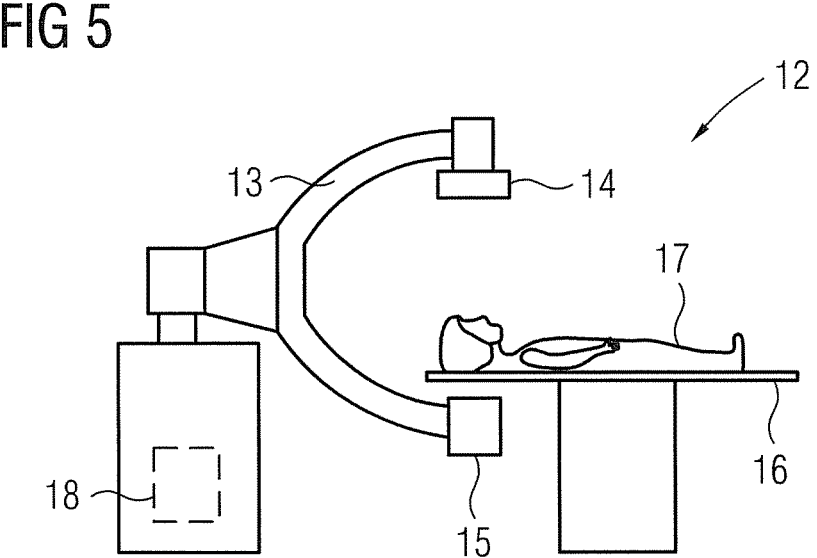
FIG. 5 shows an X-ray apparatus according to the invention.

Finally, FIG. 5 shows an X-ray apparatus 12 according to the invention. This comprises a C-arm 13 on which are disposed opposite each other an X-ray tube assembly 14 and an X-ray detector 15. The C-arm 13 is movable, in particular rotatable, around the object that is to be recorded, in this case for example a patient 17 lying on a patient table 16. A control device 18 is provided for the purpose of controlling the operation of the X-ray apparatus 12 and is also embodied for performing the method according to the invention, as has just been described.

The invention claimed is:

1. A method for reconstructing a three-dimensional image dataset of an object, comprising:
   recording a plurality of projection images for a recording geometry using different recording parameters by an X-ray apparatus, wherein the recording geometry is defined by a specified geometric position and orientation of an X-ray tube assembly and an X-ray detector of the X-ray apparatus; and
   reconstructing the three-dimensional image dataset from the projection images,
   wherein teh projection images are combined to form at least two combination images,
   wherein at least two reconstruction datasets are determined from the at least two combination images, and
   wherein the at least two reconstruction datasets are fused for reconstructing the three-dimensional images dataset.

2. The method as claimed in claim 1, wherein a predetermined number of the projection images are recorded for the recording geometry.

3. The method as claimed in claim 2, wherein the predetermined number of the projection images comprises 30 to 50 images.

4. The method as claimed in claim 1, wherein a number of the projection images to be recorded for the recording geometry are adaptively determined during the recording based on a dosage measurement and/or an image analysis of a first recorded projection image.

5. The method as claimed in claim 1, wherein a number of the projection images to be recorded for the recording geometry are adaptively determined during the recording based on a path length through the object in the recording geometry.

6. The method as claimed in claim 1, wherein the projection images are recorded using different X-ray spectra, and/or exposure times, and/or filtering parameters.

7. The method as claimed in claim 1, wherein the projection images are recorded during a single recording period in which a recording arrangement of the X-ray apparatus remains in the recording geometry and/or during a plurality of passes of the recording arrangement through the recording geometry.

8. The method as claimed in claim 1, wherein the fusion is performed based on a local noise and/or a local image structure.

9. The method as claimed in claim 1, wherein the projection images are combined by linear combination.

10. The method as claimed in claim 9, wherein different coefficients of the linear combination are used for the projection images or image regions or pixels.

11. The method as claimed in claim 10, wherein the coefficients of the linear combination are selected by an optimization algorithm with regard to a minimized variance of image data of the combination images.

12. The method as claimed in claim 1, further comprising:
   wavelet decomposing the combination images;

subdividing structures determined by the wavelet decomposition and described by wavelet coefficients in the structures by a correlation analysis; and generating a further combination image using the wavelet coefficients.

13. The method as claimed in claim 1, further comprising:

wavelet decomposing the reconstruction datasets;

subdividing structures determined by the wavelet decomposition and described by wavelet coefficients in the structures by a correlation analysis, and reconstructing the three-dimensional image dataset using the wavelet coefficients.

14. An X-ray apparatus, comprising:

a C-arm for recording a plurality of projection images for a recording geometry using different recording parameters, wherein the recording geometry is defined by a specified geometric position and orientation of an X-ray tube assembly and an X-ray detector of the C-arm; and a control device that reconstructs a three-dimensional image dataset from the projection images, wherein the projection images are combined to form at least two combination images, wherein at least reconstruction datasets are determined from the at least two combination images, and wherein the at least two reconstruction datasets are fused for reconstructing the three-dimensional image dataset.

* * * * *